United States Patent [19]

Pasteris

[11] Patent Number: 4,795,485

[45] Date of Patent: Jan. 3, 1989

[54] PHENYL-SUBSTITUTED SULFONAMIDES

[75] Inventor: Robert J. Pasteris, Wilmington, Del.

[73] Assignee: E. I. Du Pont De Nemours and Company, Wilmington, Del.

[21] Appl. No.: 35,931

[22] Filed: Apr. 8, 1987

Related U.S. Application Data

[63] Continuation of Ser. No. 705,832, Mar. 1, 1985, abandoned, which is a continuation-in-part of Ser. No. 612,659, May 21, 1984, abandoned.

[51] Int. Cl.$^4$ .................. C07D 409/12; C07D 407/12; A01N 43/66
[52] U.S. Cl. ........................................... 71/90; 71/91; 71/93; 544/212; 544/207
[58] Field of Search ............... 71/93, 90, 91; 544/212, 544/207

[56] References Cited

U.S. PATENT DOCUMENTS

| | | | |
|---|---|---|---|
| 4,492,596 | 1/1985 | Pasteris | 71/90 |
| 4,515,626 | 5/1985 | Szczpanski | 71/93 |
| 4,589,909 | 5/1986 | Rorer | 71/93 |
| 4,589,911 | 5/1986 | Ehrenfreund et al. | 544/207 |
| 4,634,465 | 1/1987 | Ehrenfreund et al. | 71/91 |

FOREIGN PATENT DOCUMENTS 0079683 6/1987 European Pat. Off.
001160 5/1983 Thailand.

*Primary Examiner*—John M. Ford

[57] ABSTRACT

This invention relates to 1-benzopyransulfonamides, 1-benzothiopyransulfonamides, 1-benzoxepinsulfonamides and 1-benzothiepinsulfonamides which are useful as plant growth regulants and in particular as herbicides.

15 Claims, No Drawings

PHENYL-SUBSTITUTED SULFONAMIDES

RELATED APPLICATIONS

This application is a continuation of my copending application U.S. Ser. No. 705,832, filed Mar. 1, 1985, now abandoned, which in turn is a continuation-in-part of application U.S. Ser. No. 612,659, filed May 21, 1984, now abandoned.

BACKGROUND OF THE INVENTION

This invention relates to 1-benzopyransulfonamides, 1-benzothiopyransulfonamides, 1-benzoxepinsulfonamides and 1-benzothiepinsulfonamides which are useful as plant growth regulants and in particular as herbicides.

Netherlands Pat. No. 121,788, published Sept. 15, 1966, discloses the preparation of compounds of the following Formula and their use as general or selective herbicides:

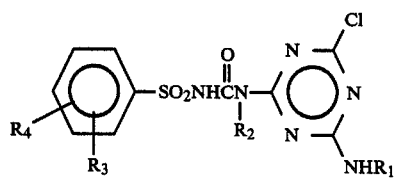

wherein $R_1$ and $R_2$ may independently be alkyl of 1-4 carbon atoms; and $R_3$ and $R_4$ may independently be hydrogen, chlorine or alkyl of 1-4 carbon atoms.

U.S. Pat. No. 3,637,366 discloses compounds having the formula:

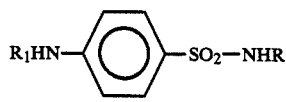

wherein $R_1$ is hydrogen or lower saturated aliphatic acyl and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

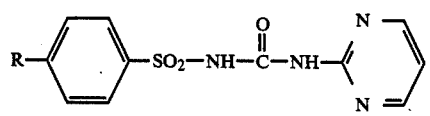

wherein

R=H, halogen, $CF_3$ or alkyl.

Logemann et al., Chem. Ab., 53, 18052g (1959), disclose a number of sulfonamides, including uracil derivatives and those having the formula:

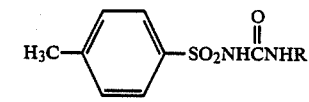

wherein

R is butyl, phenyl or

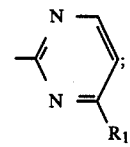

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

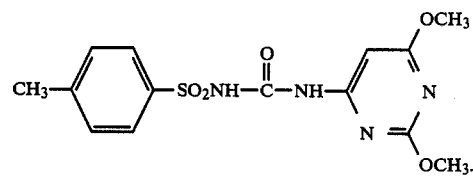

U.S. Pat. No. 4,127,405 teaches compounds which are useful for controlling weeds in wheat having the formula

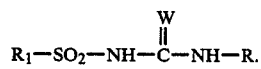

wherein

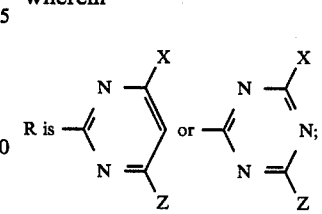

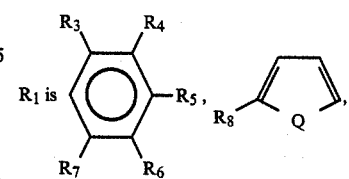

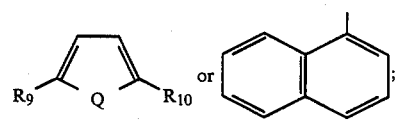

$R_3$ and $R_6$ are independently hydrogen, fluorine, chlorine, bromine, iodine, alkyl of 1-4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In addition, Unexamined European patent application No. 35,893 teaches o-alkylsulfonylbenzenesulfonylureas which are useful as herbicides.

In U.S. Pat. No. 4,391,627, there is a disclosure of herbicidal benzo[b]thiophene and benzofuransulfonylureas in which the sulfonylureido group is bonded to the heterocyclic ring.

South African patent application No. 835165 filed by Ciba-Geigy (Swiss Priority 7/16/82) discloses herbicidal sulfonylureas of the general structure shown below:

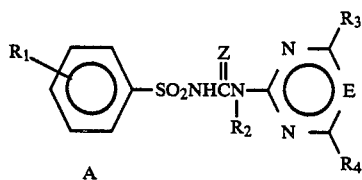

wherein

A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group.

South African patent application No. 837434 discloses herbicidal sulfonamides of formula

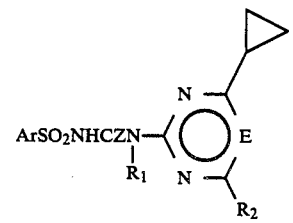

where

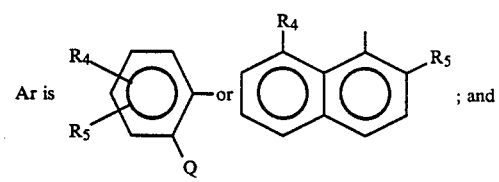

$R_2$ is halogen, $C_1$–$C_3$ alkyl, $C_1$–$C_3$ haloalkyl, $C_1$–$C_3$ alkoxy, $C_1$–$C_3$ haloalkoxy, amino, $C_1$–$C_3$ alkylamino, di($C_1$–$C_3$ alkyl)amino, $C_3$–$C_6$ cycloalkyl or $C_2$–$C_6$ alkoxyalkyl.

EP-A-79,683, published May 25, 1983, discloses herbicidal sulfonamides of formula

where

J is various benzofuran, benzothiophene, 1-benzopyran, 1-benzothiopyran, 1-benzoxepin and 1-benzothiepin moieties;

X is H, $CH_3$, $OCH_3$ or Cl;

Y is $CH_3$, $OCH_3$, $OCH_2CH_3$, $CH_2OCH_3$, $CH_2CH_3$, $NH_2$, $NHCH_3$ or $N(CH_3)_2$; and Z is CH or N.

Undesired vegetation can cause substantial damage to useful crops, especially agricultural products that satisfy man's basic food and fiber needs, such as cotton, rice, corn, wheat, soybean and the like. Although a wide variety of materials are available which can be used for killing or inhibiting (controlling) the growth of undesired vegetation the need exists for still more effective herbicides that destroy or control weeds without causing significant damage to useful crops.

SUMMARY OF THE INVENTION

This invention relates to compounds of Formula I, agricultural compositions containing them and their method-of-use as general or selective pre-emergent or post-emergent herbicides or plant growth regulants.

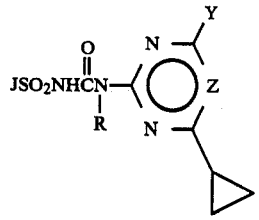

wherein

J is

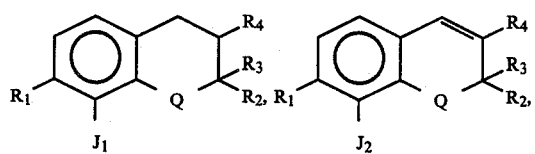

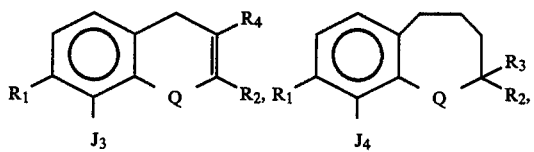

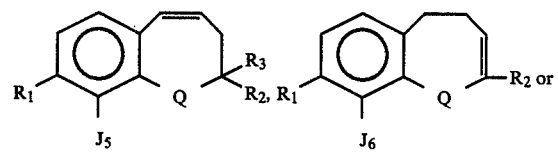

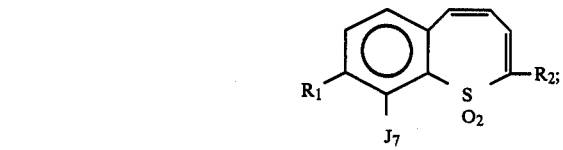

Q is O, S or $SO_2$;
R is H or $CH_3$;
$R_1$ is H, $CH_3$, $OCH_3$, Cl, Br, $CO_2R_5$, $SO_2R_6$, $OSO_2R_7$ or $SO_2NR_8R_9$;
$R_4$ is H or $CH_3$;
$R_2$ and $R_3$ are independently H or $C_1-C_3$ alkyl;
$R_5$ is $C_1-C_3$ alkyl, $CH_2CH=CH_2$, $CH_2CH_2OCH_3$ or $CH_2CH_2Cl$;
$R_6$ is $C_1-C_3$ alkyl;
$R_7$ is $C_1-C_3$ alkyl or $CF_3$;
$R_8$ and $R_9$ are independently $C_1-C_2$ alkyl;
Y is $CH_3$, $OCH_3$, $OC_2H_5$, $CH_2OCH_3$, $NHCH_3$ or $N(CH_3)_2$; and
Z is CH or N;
and their agriculturally suitable salts; provided that:
(1) the total number of carbon atoms in $R_2$ and $R_3$ is less than or equal to 3;
(2) in Formula $J_2$, when $R_2$ and $R_3$ are other than H, then $R_4$ is H;
(3) in Formula $J_3$, when $R_2$ is other than H, then $R_4$ is H;
(4) when Q is S, then $R_1$ is not $SO_2NR_8R_9$;
(5) in Formulae $J_3$ and $J_6$, Q may not be O; and
(6) in Formula $J_7$, $R_1$ is not $CH_3$.

Preferred for reasons of their higher herbicidal activity, greater plant growth regulant activity, or more favorable ease of synthesis are:
(1) Compounds of Formula I where J is $J_1$ or $J_4$.
(2) Compounds of preferred 1 where R is H and $R_1$ is H, $CH_3$, $OCH_3$, CL, $CO_2(C_1-C_2$ alkyl) or $SO_2(C_1-C_2$ alkyl).
(3) Compounds of preferred 4 where Y is $CH_3$ or $OCH_3$.
(4) Compounds of preferred 3 where J is $J_1$, $R_1$ is H, $CH_3$, $OCH_3$ or Cl, and Y is $CH_3$ or $OCH_3$.

DETAILED DESCRIPTION OF THE INVENTION

Synthesis

The compounds of Formula (I) can be prepared by methods described below in Equations 1, 2, 3, 4 and 5.

As shown in Equation 1, compounds of Formula (I) can be prepared by reacting a sulfonylcarbamate of Formula (II) with an appropriate amine of Formula (III). J, Y, Z and R are as previously defined.

Equation 1

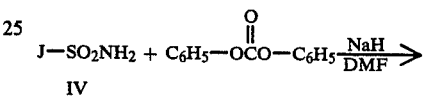

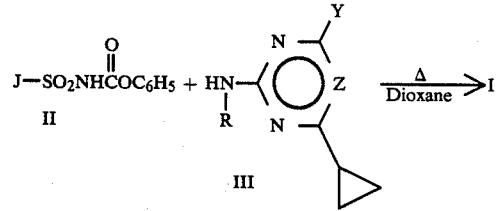

The reaction is carried out at 50°–100° C. in a solvent such as dioxane for ½ to 24 hours as taught in EPO Publication No. 44807. The required carbamates (II) are prepared by reacting the corresponding sulfonamides (IV) with diphenylcarbonate in the presence of a strong base.

Alternatively, as shown in Equation 2, compounds (I), where $R_1$ is other than $CO_2R_5$, can be prepared by reacting sulfonamides of Formula (IV) with an appropriate methylcarbamate of Formula (V) in the presence of an equimolar amount of trimethylaluminum.

Equation 2

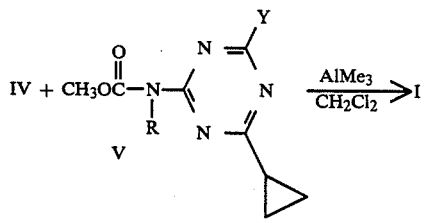

The reaction is carried out at 25° to 40° C. in a solvent such as methylene chloride for 10 to 96 hours under an inert atmosphere as taught in U.S. Ser. No. 337,934.

The compounds of Formula (I) where J is $J_1$, $J_4$ and $J_7$ for all values of Q and $J_2$, $J_3$, $J_5$ and $J_6$ when Q is $SO_2$ can be prepared by reacting sulfonylisocyanates of Formula (VI) with an appropriate amine of Formula (III) as shown in Equation 3.

Equation 3

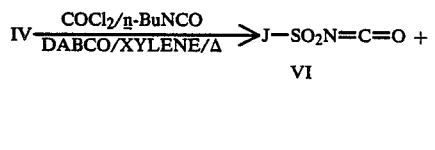

The reaction is carried out at 25° to 40° C. in an inert aprotic solvent such as methylene chloride for 0.5 to 24 hours as taught in U.S. Pat. No. 4,127,405. The intermediate sulfonylisocyanates (VI) can be prepared from the appropriate sulfonamides (IV) by the reaction with phosgene, in the presence n-butylisocyanate and a tertiary amine catalyst, at reflux in a solvent such as xylene by the method of U.S. Pat. No. 4,238,621.

Alternatively, the sulfonylisocyanates can be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst as reflux in xylene solvent. The method is similar to a procedure taught by Ulrich and Sayigh, *Newer Methods of Preparative Organic Chemistry*, Vol. VI, p. 223–241, Academic Press, New York and London, W. Foerst Ed.

The compounds of Formula (I) can also be prepared by reacting sulfonamides of Formula (IV) with an appropriate phenylcarbamate of Formula (VII) in the presence of an equimolar amount of a base such as 1,5-diazobicyclo[5.4.0]undec-5-ene (DBU), as shown in Equation 4.

Equation 4

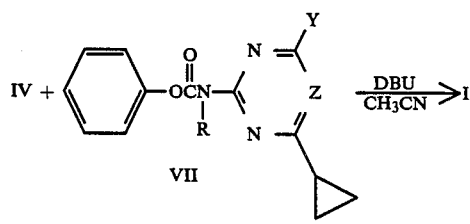

The reaction is carried out at ambient temperature in an inert solvent such as acetonitrile or dioxane as taught in South African patent application No. 825671 and South African patent application No. 825045.

Finally, the compounds of Formula (I) where $J_1$, $J_2$, $J_4$, $J_5$ and $J_7$ can be prepared by reacting sulfonylchlorides of Formula VIII with isocyanate anion in the presence of an appropriate amine of Formula III as shown in Equation 5.

Equation 5

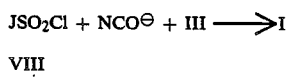

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of sulfonyl chloride of Formula VIII and at least one equivalent of heterocyclic amine of Formula III in a similar suitable organic solvent at 20°–40° C.

The sulfonamides of Formula (IV) in Equations 1, 2, 3 and 4 and the sulfonyl chlorides of Formula (VIII) in Equation 5 are important intermediates for the preparation of the compounds of this invention. The synthesis of the required sulfonamide and sulfonyl chloride intermediates are described in Equations 6, 7 and 8.

As shown in Equation 6, sulfonamides of Formula IV, where J is $J_1$, $J_2$, $J_4$, $J_5$ and $J_7$ for all Q, can be prepared from the corresponding sulfonyl chlorides of Formula VIII.

Equation 6

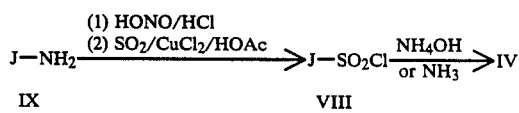

The preparation of sulfonamides from ammonium hydroxide and sulfonyl chlorides is widely reported in the literature, e.g., Crossley et al., *J. Am. Chem. Soc.*, 60, 2223 (1938) and Pailer, *Monatsh.*, 92, 677 (1961). Preparation utilizing the reaction of sulfonyl chlorides with an excess of anhydrous ammonia at 0° C. in ethyl ether or chlorobutane is also known.

The sulfonyl chlorides VIII can be prepared from the appropriate amine IX by diazotization with sodium nitrite in HCl, followed by reaction of the diazonium salt with sulfur dioxide and cupric chloride in acetic acid analogous to the teachings of Yale and Sowinski, *J. Org. Chem.*, 25, 1824 (1960).

Alternatively, sulfonyl chlorides of Formula VIII can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours as disclosed by the teachings of Unexamined European patent application No. 64,804.

Sulfonamides of Formula IVa, where n is 1 or 2, are prepared from their corresponding saturated analogs IVb as shown in Equation 7. $R_1$, $R_2$, and $R_4$ are as previously defined. When n is 2, $R_4$ is H.

Equation 7

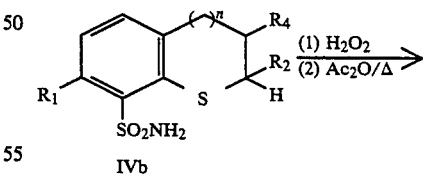

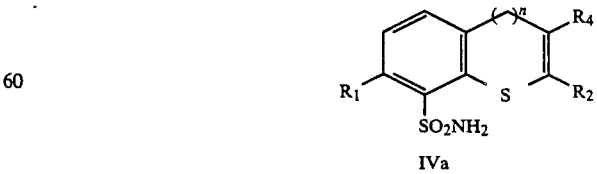

The reaction is carried out by contacting the saturated sulfide with one equivalent of a suitable oxidizing agent such as hydrogen peroxide in a solvent such as acetic acid to produce the corresponding sulfoxide. The sulfoxide is then heated with acetic anhydride with or without a cosolvent at 50° to 140° C. for 2 to 24 hours. This is similar to the method taught by Parham and Koncos, *J. Amer. Chem. Soc.*, 83, 4034 (1961) for the preparation of 4H-1-benzothiopyran.

Sulfonamides of Formula IVc where n is 0 or 1 can also be prepared from the corresponding saturated analogs IVd by the two step sequence shown in Equation 8. $R_1$, $R_2$, $R_3$, $R_4$ and Q are as previously described except that $R_1$ is not $CH_3$. When n is 1, $R_4$ is H.

Equation 8

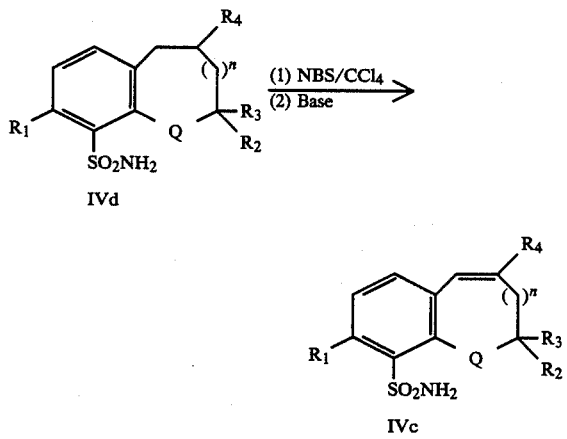

The first step involves benzylic bromination by N-bromosuccinimide in refluxing carbon tetrachloride to give a monobromo derivative. The monobromide is dehydrobrominated in the second step by contacting with a suitable base such as DABCO or ethoxide in an inert solvent such as benzene. This method has been used to prepare 2H-1-benzopyran from dihydrobenzopyran (Clemo and Ghatge, *J. Chem. Soc.*, 4347 (1955)).

Applying the above procedure a second time to the compounds IVc where n is 1, Q is $SO_2$ and $R_3$ is H will provide sulfonamides IV where J is $J_7$, as taught by Traynelis and Love, *J. Org. Chem.*, 26, 2728 (1961).

Finally, sulfonamides of Formula IV where Q is $SO_2$ can be prepared from the appropriate sulfonamides IV where Q is S by a variety of standard literature procedures with m-chloroperbenzoic acid (Johnson et. al., *Tetrahedron* 25, 5649 (1969), or with aqueous hydrogen peroxide in acetic acid (Bordwell et. al., *J. Amer. Chem. Soc.*, 77, 1141 (1955)).

The amines of Formula IX in Equation 4, where J is $J_1$, $J_2$, $J_4$, $J_5$ and $J_7$ for all Q, can be prepared by methods taught in European patent application No. 79,683 (published May 25, 1983) and by methods known in the art.

The amines of Formula III in Equation 1, 3 and 5 and the carbamates of Formula VII in Equation 4 are also important intermediates for the preparation of the compounds of this invention. South African patent application No. 837,434 (published Oct. 5, 1983) describes methods for the synthesis of cyclopropyl pyrimidines and triazines substituted by such groups as alkyl, alkoxy, alkoxyalkyl, alkylamino and dialkylamino. Such compounds may also be made by methods known to those skilled in the art.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

EXAMPLE 1

N-[(4-cyclopropyl-6-methoxy-1,3,5-triazin-2-yl)aminocarbonyl]-3,4-dihydro-2H-1-benzothiopyran-8-sulfonamide, 1,1-dioxide 0.42 g of 2-amino-4-cyclopropyl-6-methoxytriazine is added to a solution of 1.3 g of 3,4-dihydro-2H-1-benzothiopyran-8-sulfonylisocyanate, 1,1-dioxide in 20 ml of dry methylene chloride and the mixture is stirred for 16 hours at 25° C. The solvent is removed by evaporation under reduced pressure and the residue is triturated with 1-chlorobutane to give the desired urea.

Using the procedure of Example 1, the following compounds may be prepared.

TABLE I

| | | | | Formula I | | | | | m.p. |
|---|---|---|---|---|---|---|---|---|---|
| J | Q | R | $R_1$ | $R_2$ | $R_3$ | $R_4$ | Y | Z | (°C.) |
| $J_1$ | O | H | H | $CH_3$ | H | H | $CH_3$ | N | |
| $J_1$ | O | H | H | $CH_3$ | H | H | $OCH_3$ | N | |
| $J_1$ | O | H | H | $CH_3$ | H | H | $OCH_2CH_3$ | N | |
| $J_1$ | O | H | H | $CH_3$ | H | H | $CH_2OCH_3$ | N | |
| $J_1$ | O | H | H | $CH_3$ | H | H | $NHCH_3$ | N | |
| $J_1$ | O | H | H | $CH_3$ | H | H | $N(CH_3)_2$ | N | |
| $J_1$ | O | H | H | $CH_3$ | H | H | $CH_3$ | CH | |
| $J_1$ | O | H | H | $CH_3$ | H | H | $OCH_3$ | CH | |
| $J_1$ | O | H | H | $CH_3$ | H | H | $OCH_2CH_3$ | CH | |
| $J_1$ | O | H | H | $CH_3$ | H | H | $CH_2OCH_3$ | CH | |
| $J_1$ | O | H | H | $CH_3$ | H | H | $NHCH_3$ | CH | |

TABLE I-continued

Formula I

| J | Q | R | R₁ | R₂ | R₃ | R₄ | Y | Z | m.p. (°C.) |
|---|---|---|----|----|----|----|----|----|-----------|
| J₁ | O | H | H | CH₃ | H | H | N(CH₃)₂ | CH | |
| J₁ | O | CH₃ | H | CH₃ | H | H | OCH₃ | N | |
| J₁ | O | CH₃ | H | CH₃ | H | H | OCH₃ | CH | |
| J₁ | O | H | CH₃ | CH₃ | H | H | OCH₃ | N | |
| J₁ | O | H | CH₃ | CH₃ | H | H | OCH₂CH₃ | N | |
| J₁ | O | H | OCH₃ | CH₃ | H | H | OCH₃ | N | |
| J₁ | O | H | OCH₃ | CH₃ | H | H | OCH₂CH₃ | N | |
| J₁ | O | H | Cl | CH₃ | H | H | OCH₃ | N | |
| J₁ | O | H | Cl | CH₃ | H | H | OCH₂CH₃ | N | |
| J₁ | O | H | Br | CH₃ | H | H | OCH₃ | N | |
| J₁ | O | H | CO₂CH₃ | CH₃ | H | H | OCH₃ | N | |
| J₁ | O | H | SO₂CH₃ | CH₃ | H | H | OCH₃ | N | |
| J₁ | O | H | SO₂CH₂CH₃ | CH₃ | H | H | OCH₃ | N | |
| J₁ | O | H | OSO₂CH₃ | CH₃ | H | H | OCH₃ | N | |
| J₁ | O | H | OSO₂CH₂CH₃ | CH₃ | H | H | OCH₃ | N | |
| J₁ | O | H | SO₂N(CH₃)₂ | CH₃ | H | H | OCH₃ | N | |
| J₁ | O | H | H | H | H | H | OCH₃ | N | 188–191 |
| J₁ | O | H | H | H | H | H | OCH₂CH₃ | N | |
| J₁ | O | H | H | H | H | H | OCH₃ | CH | |
| J₁ | O | H | H | CH₃ | CH₃ | H | OCH₃ | N | |
| J₁ | O | H | H | CH₃ | CH₃ | H | OCH₂CH₃ | N | |
| J₁ | O | H | H | CH₃ | CH₃ | H | OCH₃ | CH | |
| J₁ | O | H | H | CH₂CH₃ | H | H | OCH₃ | N | |
| J₁ | O | H | H | CH₂CH₂CH₃ | H | H | OCH₃ | N | |
| J₁ | O | H | H | CH₂CH₂ | CH₃ | H | OCH₃ | N | |
| J₁ | O | H | OCH₃ | CH₃ | CH₃ | H | OCH₃ | N | |
| J₁ | O | H | Cl | CH₃ | CH₃ | H | OCH₃ | N | |
| J₁ | O | H | H | CH₃ | H | CH₃ | OCH₃ | N | |
| J₁ | O | H | H | CH₃ | H | CH₃ | OCH₃ | CH | |
| J₁ | O | H | H | CH₂CH₃ | H | CH₃ | OCH₃ | N | |
| J₁ | O | H | Cl | CH₃ | H | CH₃ | OCH₃ | N | |
| J₁ | S | H | H | CH₃ | H | H | CH₃ | N | |
| J₁ | S | H | H | CH₃ | H | H | OCH₃ | N | |
| J₁ | S | H | H | CH₃ | H | H | OCH₂CH₃ | N | |
| J₁ | S | H | H | CH₃ | H | H | CH₂OCH₃ | N | |
| J₁ | S | H | H | CH₃ | H | H | NHCH₃ | N | |
| J₁ | S | H | H | CH₃ | H | H | N(CH₃)₂ | N | |
| J₁ | S | H | H | CH₃ | H | H | CH₃ | CH | |
| J₁ | S | H | H | CH₃ | H | H | OCH₃ | CH | |
| J₁ | S | H | H | CH₃ | H | H | OCH₂CH₃ | CH | |
| J₁ | S | H | H | CH₃ | H | H | CH₂OCH₃ | CH | |
| J₁ | S | H | H | CH₃ | H | H | NHCH₃ | CH | |
| J₁ | S | H | H | CH₃ | H | H | N(CH₃)₂ | CH | |
| J₁ | S | CH₃ | H | CH₃ | H | H | OCH₃ | N | |
| J₁ | S | CH₃ | H | CH₃ | H | H | OCH₃ | CH | |
| J₁ | S | H | CH₃ | CH₃ | H | H | OCH₃ | N | |
| J₁ | S | H | CH₃ | CH₃ | H | H | OCH₂CH₃ | N | |
| J₁ | S | H | OCH₃ | CH₃ | H | H | OCH₃ | N | |
| J₁ | S | H | OCH₃ | CH₃ | H | H | OCH₂CH₃ | N | |
| J₁ | S | H | Cl | CH₃ | H | H | OCH₃ | N | |
| J₁ | S | H | Cl | CH₃ | H | H | OCH₂CH₃ | N | |
| J₁ | S | H | Br | CH₃ | H | H | OCH₃ | N | |
| J₁ | S | H | CO₂CH₃ | CH₃ | H | H | OCH₃ | N | |
| J₁ | S | H | SO₂CH₃ | CH₃ | H | H | OCH₃ | N | |
| J₁ | S | H | SO₂CH₂CH₃ | CH₃ | H | H | OCH₃ | N | |
| J₁ | S | H | OSO₂CH₃ | CH₃ | H | H | OCH₃ | N | |
| J₁ | S | H | OSO₂CH₂CH₃ | CH₃ | H | H | OCH₃ | N | |
| J₁ | S | H | H | H | H | H | OCH₃ | N | |
| J₁ | S | H | H | H | H | H | OCH₂CH₃ | N | |
| J₁ | S | H | H | H | H | H | OCH₃ | CH | |
| J₁ | S | H | H | CH₃ | CH₃ | H | OCH₃ | N | |
| J₁ | S | H | H | CH₃ | CH₃ | H | OCH₂CH₃ | N | |
| J₁ | S | H | H | CH₃ | CH₃ | H | OCH₃ | CH | |
| J₁ | S | H | H | CH₂CH₃ | H | H | OCH₃ | N | |
| J₁ | S | H | H | CH₂CH₂CH₃ | H | H | OCH₃ | N | |
| J₁ | S | H | H | CH₂CH₂ | CH₃ | H | OCH₃ | N | |
| J₁ | S | H | OCH₃ | CH₃ | CH₃ | H | OCH₃ | N | |
| J₁ | S | H | Cl | CH₃ | CH₃ | H | OCH₃ | N | |
| J₁ | S | H | H | CH₃ | H | CH₃ | OCH₃ | N | |
| J₁ | S | H | H | CH₃ | H | CH₃ | OCH₃ | CH | |
| J₁ | S | H | H | CH₂CH₃ | H | CH₃ | OCH₃ | N | |
| J₁ | S | H | Cl | CH₃ | H | CH₃ | OCH₃ | N | |
| J₁ | SO₂ | H | H | CH₃ | H | H | CH₃ | N | |
| J₁ | SO₂ | H | H | CH₃ | H | H | OCH₃ | N | |
| J₁ | SO₂ | H | H | CH₃ | H | H | OCH₂CH₃ | N | |
| J₁ | SO₂ | H | H | CH₃ | H | H | CH₂OCH₃ | N | |
| J₁ | SO₂ | H | H | CH₃ | H | H | NHCH₃ | N | |
| J₁ | SO₂ | H | H | CH₃ | H | H | N(CH₃)₂ | N | |
| J₁ | SO₂ | H | H | CH₃ | H | H | CH₃ | CH | |

TABLE I-continued

Formula I

| J | Q | R | $R_1$ | $R_2$ | $R_3$ | $R_4$ | Y | Z | m.p. (°C.) |
|---|---|---|---|---|---|---|---|---|---|
| $J_1$ | $SO_2$ | H | H | $CH_3$ | H | H | $OCH_3$ | CH | |
| $J_1$ | $SO_2$ | H | H | $CH_3$ | H | H | $OCH_2CH_3$ | CH | |
| $J_1$ | $SO_2$ | H | H | $CH_3$ | H | H | $CH_2OCH_3$ | CH | |
| $J_1$ | $SO_2$ | H | H | $CH_3$ | H | H | $NHCH_3$ | CH | |
| $J_1$ | $SO_2$ | H | H | $CH_3$ | H | H | $N(CH_3)_2$ | CH | |
| $J_1$ | $SO_2$ | $CH_3$ | H | $CH_3$ | H | H | $OCH_3$ | N | |
| $J_1$ | $SO_2$ | $CH_3$ | H | $CH_3$ | H | H | $OCH_3$ | CH | |
| $J_1$ | $SO_2$ | H | $CH_3$ | $CH_3$ | H | H | $OCH_3$ | N | |
| $J_1$ | $SO_2$ | H | $CH_3$ | $CH_3$ | H | H | $OCH_2CH_3$ | N | |
| $J_1$ | $SO_2$ | H | $OCH_3$ | $CH_3$ | H | H | $OCH_3$ | N | |
| $J_1$ | $SO_2$ | H | $OCH_3$ | $CH_3$ | H | H | $OCH_2CH_3$ | N | |
| $J_1$ | $SO_2$ | H | Cl | $CH_3$ | H | H | $OCH_3$ | N | |
| $J_1$ | $SO_2$ | H | Cl | $CH_3$ | H | H | $OCH_2CH_3$ | N | |
| $J_1$ | $SO_2$ | H | Br | $CH_3$ | H | H | $OCH_3$ | N | |
| $J_1$ | $SO_2$ | H | $CO_2CH_3$ | $CH_3$ | H | H | $OCH_3$ | N | |
| $J_1$ | $SO_2$ | H | $SO_2CH_3$ | $CH_3$ | H | H | $OCH_3$ | N | |
| $J_1$ | $SO_2$ | H | $SO_2CH_2CH_3$ | $CH_3$ | H | H | $OCH_3$ | N | |
| $J_1$ | $SO_2$ | H | $OSO_2CH_3$ | $CH_3$ | H | H | $OCH_3$ | N | |
| $J_1$ | $SO_2$ | H | $OSO_2CH_2CH_3$ | $CH_3$ | H | H | $OCH_3$ | N | |
| $J_1$ | $SO_2$ | H | H | H | H | H | $OCH_3$ | N | |
| $J_1$ | $SO_2$ | H | H | H | H | H | $OCH_2CH_3$ | N | |
| $J_1$ | $SO_2$ | H | H | H | H | H | $OCH_3$ | CH | |
| $J_1$ | $SO_2$ | H | H | $CH_3$ | $CH_3$ | H | $OCH_3$ | N | |
| $J_1$ | $SO_2$ | H | H | $CH_3$ | $CH_3$ | H | $OCH_2CH_3$ | N | |
| $J_1$ | $SO_2$ | H | H | $CH_3$ | $CH_3$ | H | $OCH_3$ | CH | |
| $J_1$ | $SO_2$ | H | H | $CH_2CH_3$ | H | H | $OCH_3$ | N | |
| $J_1$ | $SO_2$ | H | H | $CH_2CH_2CH_3$ | H | H | $OCH_3$ | N | |
| $J_1$ | $SO_2$ | H | H | $CH_2CH_2$ | $CH_3$ | H | $OCH_3$ | N | |
| $J_1$ | $SO_2$ | H | $OCH_3$ | $CH_3$ | $CH_3$ | H | $OCH_3$ | N | |
| $J_1$ | $SO_2$ | H | Cl | $CH_3$ | $CH_3$ | H | $OCH_3$ | N | |
| $J_1$ | $SO_2$ | H | H | $CH_3$ | H | $CH_3$ | $OCH_3$ | N | |
| $J_1$ | $SO_2$ | H | H | $CH_3$ | H | $CH_3$ | $OCH_3$ | CH | |
| $J_1$ | $SO_2$ | H | H | $CH_2CH_3$ | H | $CH_3$ | $OCH_3$ | N | |
| $J_1$ | $SO_2$ | H | Cl | $CH_3$ | H | $CH_3$ | $OCH_3$ | N | |
| $J_4$ | O | H | H | $CH_3$ | H | — | $CH_3$ | N | |
| $J_4$ | O | H | H | $CH_3$ | H | — | $OCH_3$ | N | |
| $J_4$ | O | H | H | $CH_3$ | H | — | $OCH_2CH_3$ | N | |
| $J_4$ | O | H | H | $CH_3$ | H | — | $CH_2OCH_3$ | N | |
| $J_4$ | O | H | H | $CH_3$ | H | — | $NHCH_3$ | N | |
| $J_4$ | O | H | H | $CH_3$ | H | — | $N(CH_3)_2$ | N | |
| $J_4$ | O | H | H | $CH_3$ | H | — | $CH_3$ | CH | |
| $J_4$ | O | H | H | $CH_3$ | H | — | $OCH_3$ | CH | |
| $J_4$ | O | H | H | $CH_3$ | H | — | $OCH_2CH_3$ | CH | |
| $J_4$ | O | H | H | $CH_3$ | H | — | $CH_2OCH_3$ | CH | |
| $J_4$ | O | H | H | $CH_3$ | H | — | $NHCH_3$ | CH | |
| $J_4$ | O | H | H | $CH_3$ | H | — | $N(CH_3)_2$ | CH | |
| $J_4$ | O | $CH_3$ | H | $CH_3$ | H | — | $OCH_3$ | N | |
| $J_4$ | O | $CH_3$ | H | $CH_3$ | H | — | $OCH_3$ | CH | |
| $J_4$ | O | H | $CH_3$ | $CH_3$ | H | — | $OCH_3$ | N | |
| $J_4$ | O | H | $CH_3$ | $CH_3$ | H | — | $OCH_2CH_3$ | N | |
| $J_4$ | O | H | $OCH_3$ | $CH_3$ | H | — | $OCH_3$ | N | |
| $J_4$ | O | H | $OCH_3$ | $CH_3$ | H | — | $OCH_2CH_3$ | N | |
| $J_4$ | O | H | Cl | $CH_3$ | H | — | $OCH_3$ | N | |
| $J_4$ | O | H | Cl | $CH_3$ | H | — | $OCH_2CH_3$ | N | |
| $J_4$ | O | H | Br | $CH_3$ | H | — | $OCH_3$ | N | |
| $J_4$ | O | H | $CO_2CH_3$ | $CH_3$ | H | — | $OCH_3$ | N | |
| $J_4$ | O | H | $SO_2CH_3$ | $CH_3$ | H | — | $OCH_3$ | N | |
| $J_4$ | O | H | $SO_2CH_2CH_3$ | $CH_3$ | H | — | $OCH_3$ | N | |
| $J_4$ | O | H | $OSO_2CH_3$ | $CH_3$ | H | — | $OCH_3$ | N | |
| $J_4$ | O | H | $OSO_2CH_2CH_3$ | $CH_3$ | H | — | $OCH_3$ | N | |
| $J_4$ | O | H | $SO_2N(CH_3)_2$ | $CH_3$ | H | — | $OCH_3$ | N | |
| $J_4$ | O | H | H | H | H | — | $OCH_3$ | N | |
| $J_4$ | O | H | H | H | H | — | $OCH_2CH_3$ | N | |
| $J_4$ | O | H | H | H | H | — | $OCH_3$ | CH | |
| $J_4$ | O | H | H | $CH_3$ | $CH_3$ | — | $OCH_3$ | N | |
| $J_4$ | O | H | H | $CH_3$ | $CH_3$ | — | $OCH_2CH_3$ | N | |
| $J_4$ | O | H | H | $CH_3$ | $CH_3$ | — | $OCH_3$ | CH | |
| $J_4$ | O | H | H | $CH_2CH_3$ | H | — | $OCH_3$ | N | |
| $J_4$ | O | H | H | $CH_2CH_2CH_3$ | H | — | $OCH_3$ | N | |
| $J_4$ | O | H | H | $CH_2CH_2$ | $CH_3$ | — | $OCH_3$ | N | |
| $J_4$ | O | H | $OCH_3$ | $CH_3$ | $CH_3$ | — | $OCH_3$ | N | |
| $J_4$ | O | H | Cl | $CH_3$ | $CH_3$ | — | $OCH_3$ | N | |
| $J_4$ | S | H | H | $CH_3$ | H | — | $CH_3$ | N | |
| $J_4$ | S | H | H | $CH_3$ | H | — | $OCH_3$ | N | |
| $J_4$ | S | H | H | $CH_3$ | H | — | $OCH_2CH_3$ | N | |
| $J_4$ | S | H | H | $CH_3$ | H | — | $CH_2OCH_3$ | N | |
| $J_4$ | S | H | H | $CH_3$ | H | — | $NHCH_3$ | N | |
| $J_4$ | S | H | H | $CH_3$ | H | — | $N(CH_3)_2$ | N | |
| $J_4$ | S | H | H | $CH_3$ | H | — | $CH_3$ | CH | |

TABLE I-continued

Formula I

| J | Q | R | R₁ | R₂ | R₃ | R₄ | Y | Z | m.p. (°C.) |
|---|---|---|---|---|---|---|---|---|---|
| J₄ | S | H | H | CH₃ | H | — | OCH₃ | CH | |
| J₄ | S | H | H | CH₃ | H | — | OCH₂CH₃ | CH | |
| J₄ | S | H | H | CH₃ | H | — | CH₂OCH₃ | CH | |
| J₄ | S | H | H | CH₃ | H | — | NHCH₃ | CH | |
| J₄ | S | H | H | CH₃ | H | — | N(CH₃)₂ | CH | |
| J₄ | S | CH₃ | H | CH₃ | H | — | OCH₃ | N | |
| J₄ | S | CH₃ | H | CH₃ | H | — | OCH₃ | CH | |
| J₄ | S | H | CH₃ | CH₃ | H | — | OCH₃ | N | |
| J₄ | S | H | CH₃ | CH₃ | H | — | OCH₂CH₃ | N | |
| J₄ | S | H | OCH₃ | CH₃ | H | — | OCH₃ | N | |
| J₄ | S | H | OCH₃ | CH₃ | H | — | OCH₂CH₃ | N | |
| J₄ | S | H | Cl | CH₃ | H | — | OCH₃ | N | |
| J₄ | S | H | Cl | CH₃ | H | — | OCH₂CH₃ | N | |
| J₄ | S | H | Br | CH₃ | H | — | OCH₃ | N | |
| J₄ | S | H | CO₂CH₃ | CH₃ | H | — | OCH₃ | N | |
| J₄ | S | H | SO₂CH₃ | CH₃ | H | — | OCH₃ | N | |
| J₄ | S | H | SO₂CH₂CH₃ | CH₃ | H | — | OCH₃ | N | |
| J₄ | S | H | OSO₂CH₃ | CH₃ | H | — | OCH₃ | N | |
| J₄ | S | H | OSO₂CH₂CH₃ | CH₃ | H | — | OCH₃ | N | |
| J₄ | S | H | H | H | H | — | OCH₃ | N | |
| J₄ | S | H | H | H | H | — | OCH₂CH₃ | N | |
| J₄ | S | H | H | H | H | — | OCH₃ | CH | |
| J₄ | S | H | H | CH₃ | CH₃ | — | OCH₃ | N | |
| J₄ | S | H | H | CH₃ | CH₃ | — | OCH₂CH₃ | N | |
| J₄ | S | H | H | CH₃ | CH₃ | — | OCH₃ | CH | |
| J₄ | S | H | H | CH₂CH₃ | H | — | OCH₃ | N | |
| J₄ | S | H | H | CH₂CH₂CH₃ | H | — | OCH₃ | N | |
| J₄ | S | H | H | CH₂CH₂ | CH₃ | — | OCH₃ | N | |
| J₄ | S | H | OCH₃ | CH₃ | CH₃ | — | OCH₃ | N | |
| J₄ | S | H | Cl | CH₃ | CH₃ | — | OCH₃ | N | |
| J₄ | SO₂ | H | H | CH₃ | H | — | CH₃ | N | |
| J₄ | SO₂ | H | H | CH₃ | H | — | OCH₃ | N | |
| J₄ | SO₂ | H | H | CH₃ | H | — | OCH₂CH₃ | N | |
| J₄ | SO₂ | H | H | CH₃ | H | — | CH₂OCH₃ | N | |
| J₄ | SO₂ | H | H | CH₃ | H | — | NHCH₃ | N | |
| J₄ | SO₂ | H | H | CH₃ | H | — | N(CH₃)₂ | N | |
| J₄ | SO₂ | H | H | CH₃ | H | — | CH₃ | CH | |
| J₄ | SO₂ | H | H | CH₃ | H | — | OCH₃ | CH | |
| J₄ | SO₂ | H | H | CH₃ | H | — | OCH₂CH₃ | CH | |
| J₄ | SO₂ | H | H | CH₃ | H | — | CH₂OCH₃ | CH | |
| J₄ | SO₂ | H | H | CH₃ | H | — | NHCH₃ | CH | |
| J₄ | SO₂ | H | H | CH₃ | H | — | N(CH₃)₂ | CH | |
| J₄ | SO₂ | CH₃ | H | CH₃ | H | — | OCH₃ | N | |
| J₄ | SO₂ | CH₃ | H | CH₃ | H | — | OCH₃ | CH | |
| J₄ | SO₂ | H | CH₃ | CH₃ | H | — | OCH₃ | N | |
| J₄ | SO₂ | H | CH₃ | CH₃ | H | — | OCH₂CH₃ | N | |
| J₄ | SO₂ | H | OCH₃ | CH₃ | H | — | OCH₃ | N | |
| J₄ | SO₂ | H | OCH₃ | CH₃ | H | — | OCH₂CH₃ | N | |
| J₄ | SO₂ | H | Cl | CH₃ | H | — | OCH₃ | N | |
| J₄ | SO₂ | H | Cl | CH₃ | H | — | OCH₂CH₃ | N | |
| J₄ | SO₂ | H | Br | CH₃ | H | — | OCH₃ | N | |
| J₄ | SO₂ | H | CO₂CH₃ | CH₃ | H | — | OCH₃ | N | |
| J₄ | SO₂ | H | SO₂CH₃ | CH₃ | H | — | OCH₃ | N | |
| J₄ | SO₂ | H | SO₂CH₂CH₃ | CH₃ | H | — | OCH₃ | N | |
| J₄ | SO₂ | H | OSO₂CH₃ | CH₃ | H | — | OCH₃ | N | |
| J₄ | SO₂ | H | OSO₂CH₂CH₃ | CH₃ | H | — | OCH₃ | N | |
| J₄ | SO₂ | H | SO₂N(CH₃)₂ | CH₃ | H | — | OCH₃ | N | |
| J₄ | SO₂ | H | H | H | H | — | OCH₃ | N | |
| J₄ | SO₂ | H | H | H | H | — | OCH₂CH₃ | N | |
| J₄ | SO₂ | H | H | H | H | — | OCH₃ | CH | |
| J₄ | SO₂ | H | H | CH₃ | CH₃ | — | OCH₃ | N | |
| J₄ | SO₂ | H | H | CH₃ | CH₃ | — | OCH₂CH₃ | N | |
| J₄ | SO₂ | H | H | CH₃ | CH₃ | — | OCH₃ | CH | |
| J₄ | SO₂ | H | H | CH₂CH₃ | H | — | OCH₃ | N | |
| J₄ | SO₂ | H | H | CH₂CH₂CH₃ | H | — | OCH₃ | N | |
| J₄ | SO₂ | H | H | CH₂CH₂ | CH₃ | — | OCH₃ | N | |
| J₄ | SO₂ | H | OCH₃ | CH₃ | CH₃ | — | OCH₃ | N | |
| J₄ | SO₂ | H | Cl | CH₃ | CH₃ | — | OCH₃ | N | |
| J₂ | O | H | H | H | H | H | OCH₃ | N | |
| J₂ | O | H | H | CH₃ | H | H | OCH₃ | N | |
| J₂ | O | H | H | CH₃ | H | H | OCH₂CH₃ | N | |
| J₂ | O | H | H | CH₃ | CH₃ | H | OCH₃ | N | |
| J₂ | O | H | H | CH₃ | CH₃ | H | OCH₂CH₃ | N | |
| J₂ | O | H | H | CH₃ | CH₃ | H | OCH₃ | CH | |
| J₂ | O | H | Cl | CH₃ | CH₃ | H | OCH₃ | N | |
| J₂ | O | H | OCH₃ | CH₃ | CH₃ | H | OCH₃ | N | |
| J₂ | O | CH₃ | H | CH₃ | CH₃ | H | OCH₃ | N | |
| J₂ | O | H | H | H | H | CH₃ | OCH₃ | N | |
| J₂ | O | H | H | CH₂CH₃ | CH₃ | H | OCH₃ | N | |

TABLE I-continued

Formula I

| J | Q | R | $R_1$ | $R_2$ | $R_3$ | $R_4$ | Y | Z | m.p. (°C.) |
|---|---|---|---|---|---|---|---|---|---|
| $J_5$ | O | H | H | H | H | — | $OCH_3$ | N | |
| $J_5$ | O | H | H | $CH_3$ | H | — | $OCH_3$ | N | |
| $J_5$ | O | H | H | $CH_3$ | H | — | $OCH_2CH_3$ | N | |
| $J_5$ | O | H | H | $CH_3$ | H | — | $OCH_3$ | CH | |
| $J_5$ | O | H | H | $CH_3$ | H | — | $CH_3$ | CH | |
| $J_5$ | O | H | Cl | $CH_3$ | H | — | $OCH_3$ | N | |
| $J_5$ | O | H | H | $CH_3$ | $CH_3$ | — | $OCH_3$ | N | |
| $J_5$ | O | H | Cl | $CH_3$ | $CH_3$ | — | $OCH_3$ | N | |
| $J_5$ | O | H | $OCH_3$ | $CH_3$ | $CH_3$ | — | $OCH_3$ | N | |
| $J_2$ | S | H | H | H | H | H | $OCH_3$ | N | |
| $J_2$ | S | H | H | $CH_3$ | H | H | $OCH_3$ | N | |
| $J_2$ | S | H | H | $CH_3$ | H | H | $OCH_2CH_3$ | N | |
| $J_2$ | S | H | H | $CH_3$ | $CH_3$ | H | $OCH_3$ | N | |
| $J_2$ | S | H | H | $CH_3$ | $CH_3$ | H | $OCH_2CH_3$ | N | |
| $J_2$ | S | H | H | $CH_3$ | $CH_3$ | H | $OCH_3$ | CH | |
| $J_2$ | S | H | Cl | $CH_3$ | $CH_3$ | H | $OCH_3$ | N | |
| $J_2$ | S | H | $OCH_3$ | $CH_3$ | $CH_3$ | H | $OCH_3$ | N | |
| $J_2$ | S | $CH_3$ | H | $CH_3$ | $CH_3$ | H | $OCH_3$ | N | |
| $J_2$ | S | H | H | H | H | $CH_3$ | $OCH_3$ | N | |
| $J_2$ | S | H | H | $CH_2CH_3$ | $CH_3$ | H | $OCH_3$ | N | |
| $J_5$ | S | H | H | H | H | — | $OCH_3$ | N | |
| $J_5$ | S | H | H | $CH_3$ | H | — | $OCH_3$ | N | |
| $J_5$ | S | H | H | $CH_3$ | H | — | $OCH_2CH_3$ | N | |
| $J_5$ | S | H | H | $CH_3$ | H | — | $OCH_3$ | CH | |
| $J_5$ | S | H | H | $CH_3$ | H | — | $CH_3$ | CH | |
| $J_5$ | S | H | Cl | $CH_3$ | H | — | $OCH_3$ | N | |
| $J_5$ | S | H | H | $CH_3$ | $CH_3$ | — | $OCH_3$ | N | |
| $J_5$ | S | H | Cl | $CH_3$ | $CH_3$ | — | $OCH_3$ | N | |
| $J_5$ | S | H | $OCH_3$ | $CH_3$ | $CH_3$ | — | $OCH_3$ | N | |
| $J_2$ | $SO_2$ | H | H | H | H | H | $OCH_3$ | N | |
| $J_2$ | $SO_2$ | H | H | $CH_3$ | H | H | $OCH_3$ | N | |
| $J_2$ | $SO_2$ | H | H | $CH_3$ | H | H | $OCH_2CH_3$ | N | |
| $J_2$ | $SO_2$ | H | H | $CH_3$ | $CH_3$ | H | $OCH_3$ | N | |
| $J_2$ | $SO_2$ | H | H | $CH_3$ | $CH_3$ | H | $OCH_2CH_3$ | N | |
| $J_2$ | $SO_2$ | H | H | $CH_3$ | $CH_3$ | H | $OCH_3$ | CH | |
| $J_2$ | $SO_2$ | H | Cl | $CH_3$ | $CH_3$ | H | $OCH_3$ | N | |
| $J_2$ | $SO_2$ | H | $OCH_3$ | $CH_3$ | $CH_3$ | H | $OCH_3$ | N | |
| $J_2$ | $SO_2$ | $CH_3$ | H | $CH_3$ | $CH_3$ | H | $OCH_3$ | N | |
| $J_2$ | $SO_2$ | H | H | H | H | $CH_3$ | $OCH_3$ | N | |
| $J_2$ | $SO_2$ | H | H | $CH_2CH_3$ | $CH_3$ | H | $OCH_3$ | N | |
| $J_5$ | $SO_2$ | H | H | H | H | — | $OCH_3$ | N | |
| $J_5$ | $SO_2$ | H | H | $CH_3$ | H | — | $OCH_3$ | N | |
| $J_5$ | $SO_2$ | H | H | $CH_3$ | H | — | $OCH_2CH_3$ | N | |
| $J_5$ | $SO_2$ | H | H | $CH_3$ | H | — | $OCH_3$ | CH | |
| $J_5$ | $SO_2$ | H | H | $CH_3$ | H | — | $CH_3$ | CH | |
| $J_5$ | $SO_2$ | H | Cl | $CH_3$ | H | — | $OCH_3$ | N | |
| $J_5$ | $SO_2$ | H | H | $CH_3$ | $CH_3$ | — | $OCH_3$ | N | |
| $J_5$ | $SO_2$ | H | Cl | $CH_3$ | $CH_3$ | — | $OCH_3$ | N | |
| $J_5$ | $SO_2$ | H | $OCH_3$ | $CH_3$ | $CH_3$ | — | $OCH_3$ | N | |
| $J_7$ | — | H | H | H | — | — | $OCH_3$ | N | |
| $J_7$ | — | H | H | H | — | — | $OCH_3$ | CH | |
| $J_7$ | — | H | H | $CH_3$ | — | — | $OCH_3$ | N | |
| $J_7$ | — | H | Cl | $CH_3$ | — | — | $OCH_3$ | N | |
| $J_7$ | — | H | H | $CH_2CH_3$ | — | — | $OCH_3$ | N | |
| $J_7$ | — | H | H | $CH_2CH_2CH_3$ | — | — | $OCH_3$ | N | |
| $J_3$ | S | H | H | $CH_3$ | — | H | $OCH_3$ | N | |
| $J_3$ | S | H | H | H | — | H | $OCH_3$ | N | |
| $J_3$ | S | H | H | $CH_3$ | — | H | $OCH_2CH_3$ | N | |
| $J_3$ | S | H | H | $CH_3$ | — | H | $OCH_3$ | CH | |
| $J_3$ | S | H | H | $CH_3$ | — | H | $CH_2OCH_3$ | CH | |
| $J_3$ | S | H | H | $CH_2CH_3$ | — | H | $OCH_3$ | N | |
| $J_3$ | S | H | H | $CH(CH_3)_2$ | — | H | $OCH_3$ | N | |
| $J_3$ | S | H | Cl | $CH_3$ | — | H | $OCH_3$ | N | |
| $J_3$ | S | H | $OCH_3$ | $CH_3$ | — | H | $OCH_3$ | N | |
| $J_3$ | S | H | H | H | — | $CH_3$ | $OCH_3$ | N | |
| $J_6$ | S | H | H | H | — | — | $OCH_3$ | N | |
| $J_6$ | S | H | H | H | — | — | $OCH_2CH_3$ | N | |
| $J_6$ | S | H | H | H | — | — | $OCH_3$ | CH | |
| $J_6$ | S | H | H | $CH_3$ | — | — | $NHCH_3$ | N | |
| $J_6$ | S | H | H | $CH_3$ | — | — | $NH(CH_3)_2$ | N | |
| $J_6$ | S | H | H | $CH_3$ | — | — | $OCH_3$ | N | |
| $J_6$ | S | H | H | $CH_3$ | — | — | $OCH_2CH_3$ | N | |
| $J_6$ | S | H | Cl | $CH_3$ | — | — | $OCH_3$ | N | |
| $J_6$ | S | H | $CH_3$ | $CH_3$ | — | — | $OCH_3$ | N | |
| $J_6$ | S | H | H | $CH_2CH_3$ | — | — | $OCH_3$ | N | |
| $J_6$ | S | H | H | $CH(CH_3)_2$ | — | — | $OCH_3$ | N | |
| $J_6$ | S | H | H | $CH_2CH_2CH_2$ | — | — | $OCH_3$ | N | |
| $J_3$ | $SO_2$ | H | H | $CH_3$ | — | H | $OCH_3$ | N | |
| $J_3$ | $SO_2$ | H | H | H | — | H | $OCH_3$ | N | |

TABLE I-continued

Formula I

| J | Q | R | $R_1$ | $R_2$ | $R_3$ | $R_4$ | Y | Z | m.p. (°C.) |
|---|---|---|---|---|---|---|---|---|---|
| $J_3$ | $SO_2$ | H | H | $CH_3$ | — | H | $OCH_2CH_3$ | N | |
| $J_3$ | $SO_2$ | H | H | $CH_3$ | — | H | $OCH_3$ | CH | |
| $J_3$ | $SO_2$ | H | H | $CH_3$ | — | H | $CH_2OCH_3$ | CH | |
| $J_3$ | $SO_2$ | H | H | $CH_2CH_3$ | — | H | $OCH_3$ | N | |
| $J_3$ | $SO_2$ | H | H | $CH(CH_3)_2$ | — | H | $OCH_3$ | N | |
| $J_3$ | $SO_2$ | H | Cl | $CH_3$ | — | H | $OCH_3$ | N | |
| $J_3$ | $SO_2$ | H | $OCH_3$ | $CH_3$ | — | H | $OCH_3$ | N | |
| $J_3$ | $SO_2$ | H | H | H | — | $CH_3$ | $OCH_3$ | N | |
| $J_6$ | $SO_2$ | H | H | H | — | — | $OCH_3$ | N | |
| $J_6$ | $SO_2$ | H | H | H | — | — | $OCH_2CH_3$ | N | |
| $J_6$ | $SO_2$ | H | H | H | — | — | $OCH_3$ | CH | |
| $J_6$ | $SO_2$ | H | H | $CH_3$ | — | — | $NHCH_3$ | N | |
| $J_6$ | $SO_2$ | H | H | $CH_3$ | — | — | $NH(CH_3)_2$ | N | |
| $J_6$ | $SO_2$ | H | H | $CH_3$ | — | — | $OCH_3$ | N | |
| $J_6$ | $SO_2$ | H | H | $CH_3$ | — | — | $OCH_2CH_3$ | N | |
| $J_6$ | $SO_2$ | H | Cl | $CH_3$ | — | — | $OCH_3$ | N | |
| $J_6$ | $SO_2$ | H | $CH_3$ | $CH_3$ | — | — | $OCH_3$ | N | |
| $J_6$ | $SO_2$ | H | H | $CH_2CH_3$ | — | — | $OCH_3$ | N | |
| $J_6$ | $SO_2$ | H | H | $CH(CH_3)_2$ | — | — | $OCH_3$ | N | |
| $J_6$ | $SO_2$ | H | H | $CH_2CH_2CH_2$ | — | — | $OCH_3$ | N | |
| $J_1$ | O | H | $CO_2CH_2CH_2CH_3$ | $CH_3$ | H | H | $OCH_3$ | N | |
| $J_1$ | O | H | $CO_2CH_2CH=CH_2$ | $CH_3$ | H | H | $OCH_3$ | N | |
| $J_1$ | O | H | $CO_2CH_2CH_2OCH_3$ | $CH_3$ | H | H | $OCH_3$ | N | |
| $J_1$ | O | H | $CO_2CH_2CH_2Cl$ | $CH_3$ | H | H | $OCH_3$ | N | |
| $J_1$ | O | H | $SO_2CH_2CH_2CH_3$ | $CH_3$ | H | H | $OCH_3$ | N | |
| $J_1$ | O | H | $SO_2CH(CH_3)_2$ | $CH_3$ | H | H | $OCH_3$ | N | |
| $J_1$ | O | H | $OSO_2CH_2CH_2CH_3$ | $CH_3$ | H | H | $OCH_3$ | N | |
| $J_1$ | O | H | $OSO_2CH(CH_3)_2$ | $CH_3$ | H | H | $OCH_3$ | N | |
| $J_1$ | O | H | $SO_2N(CH_3)CH_2CH_3$ | $CH_3$ | H | H | $OCH_3$ | N | |
| $J_1$ | O | H | $SO_2N(CH_2CH_3)_2$ | $CH_3$ | H | H | $OCH_3$ | N | |
| $J_1$ | O | H | $OSO_2CF_3$ | $CH_3$ | H | H | $OCH_3$ | N | |
| $J_1$ | $SO_2$ | H | $CO_2CH_2CH_2CH_3$ | $CH_3$ | H | H | $OCH_3$ | N | |
| $J_1$ | $SO_2$ | H | $CO_2CH_2CH=CH_2$ | $CH_3$ | H | H | $OCH_3$ | N | |
| $J_1$ | $SO_2$ | H | $CO_2CH_2CH_2OCH_3$ | $CH_3$ | H | H | $OCH_3$ | N | |
| $J_1$ | $SO_2$ | H | $CO_2CH_2CH_2Cl$ | $CH_3$ | H | H | $OCH_3$ | N | |
| $J_1$ | $SO_2$ | H | $SO_2CH_2CH_2CH_3$ | $CH_3$ | H | H | $OCH_3$ | N | |
| $J_1$ | $SO_2$ | H | $SO_2CH(CH_3)_2$ | $CH_3$ | H | H | $OCH_3$ | N | |
| $J_1$ | $SO_2$ | H | $OSO_2CH_2CH_2CH_3$ | $CH_3$ | H | H | $OCH_3$ | N | |
| $J_1$ | $SO_2$ | H | $OSO_2CH(CH_3)_2$ | $CH_3$ | H | H | $OCH_3$ | N | |
| $J_1$ | $SO_2$ | H | $SO_2N(CH_3)CH_2CH_3$ | $CH_3$ | H | H | $OCH_3$ | N | |
| $J_1$ | $SO_2$ | H | $SO_2N(CH_2CH_3)_2$ | $CH_3$ | H | H | $OCH_3$ | N | |
| $J_1$ | $SO_2$ | H | $OSO_2CF_3$ | $CH_3$ | H | H | $OCH_3$ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE II

| | Active Ingredient | Weight Diluent(s) | Percent* Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

TABLE II-continued

| Active Ingredient | Weight Diluent(s) | Percent* Surfactant(s) |
|---|---|---|

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 2

| Wettable Powder | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

| Wettable Powder | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

| Granule | |
|---|---|
| Wettable Powder of Example 3 | 5% |
| attapulgite granules | 95% |
| (U.S.S. 20–40 mesh; 0.84–0.42 mm) | 25% |

A slurry of wettable powder containing 25% solids is sprayed on the surface of attapulgite granules in a double-cone blender. The granules are dried and packaged.

EXAMPLE 5

| Extruded Pellet | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

| Oil Suspension | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 7

| Wettable Powder | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 8

| Low Strength Granule | |
|---|---|
| N—[(4-cyclopropyl-6-methoxy-1,3,5-triazin-2-yl)amino-carbonyl]-3,4-dihydro-2H—1-benzothiopyran-8-sulfonamide, 1,1-dioxide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

| Aqueous Suspension | |
|---|---|
| N—[(4-cyclopropyl-6-methoxy-1,3,5-triazin-2-yl) aminocarbonyl]-3,4-dihydro-2H—1-benzothiopyran-8-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 10

| Solution | |
|---|---|
| N—[(4-cyclopropyl-6-methoxy-1,3,5-triazin-2-yl) aminocarbonyl]-3,4-dihydro-2H—1-benzothiopyran-8-sulfonamide, 1,1-dioxide, sodium salt | 5% |
| water | 95% |

The salt is added directly to the water with stirring to produce the solution, which may then be packaged for use.

EXAMPLE 11

| Low Strength Granule | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

| Granule | |
|---|---|
| N—[(4-cyclopropyl-6-methoxy-1,3,5-triazin-2-yl)aminocar-bonyl]-3,4-dihydro-2H—1-benzothiopyran-8-sulfonamide, 1,1-dioxide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 13

| High Strength Concentrate | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 14

| Wettable Powder | |
|---|---|
| N—[(4-cyclopropyl-6-methoxy-1,3,5-triazin-2-yl)aminocarbonyl]-3,4-dihydro-2H—benzothiopyran-8-sulfonamide, 1,1-dioxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 15

| Wettable Powder | |
|---|---|
| N—[(4-cyclopropyl-6-methoxy-1,3,5-triazin-2-yl)aminocarbonyl]-3,4-dihydro-2H—benzothiopyran-8-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 16

| Oil Suspension | |
|---|---|
| N—[(4-cyclopropyl-6-methoxy-1,3,5-triazin-2-yl)aminocarbonyl]-3,4-dihydro-2H—1-benzothiopyran-8-sulfon- | 35% |

| -continued | |
|---|---|
| Oil Suspension | |
| amide, 1,1-dioxide | |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 17

| Dust | |
|---|---|
| N—[(4-cyclopropyl-6-methoxy-1,3,5-triazin-2-yl)aminocarbonyl]-3,4-dihydro-2H—1-benzothiopyran-8-sulfonamide, 1,1-dioxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the compounds may be used to modify plant growth.

The rates of application for the compounds of the invention are determined by a number of factors, including their use as growth modifiers, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for growth modification or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were observed in greenhouse tests. The test procedures follow.

Compounds

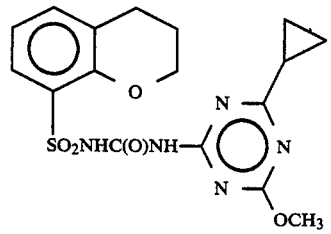

Compound 1

Test A

Seeds of crabgrass (Digitaria sp.), barnyardgrass (Echinochloa crusgalli), wild oats (Avena fatua), cheatgrass (Bromus secalinus), velvetleaf (Abutilon theophrasti), morningglory (Ipomoea sp.), cocklebur (Xanthium sp.), sorghum, corn, soybean, sugar beet, rice, wheat and nutsedge tubers (Cyperus rotundus) were planted in a growth medium and treated pre-emergence with the chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls are maintained in a greenhouse for sixteen days, after which all species were compared to controls and visually rated for response to treatment. The ratings are based on a numerical scale extending from 0=no injury, to 10=complete kill. The accompanying descriptive symbols have the following meanings:
C=chlorosis/necrosis;
E=emergence inhibition;
G=growth retardation;
H=formative effects;
U=unusual pigmentation;
X=axillary stimulation; and
6Y=abscised buds or flowers.

TABLE III

| Rate (kg/ha) | 0.05 |
|---|---|
| POSTEMERGENCE | |
| Morningglory | 3C,8H |
| Cocklebur | 5C,9G |
| Velvetleaf | 9C |
| Nutsedge | 3G |
| Crabgrass | 0 |
| Barnyardgrass | 5G |
| Cheatgrass | 0 |
| Wild Oats | 0 |
| Wheat | 0 |
| Corn | 3C,9H |
| Soybean | 3C,9H |
| Rice | 5C,9G |
| Sorghum | 4C,9H |
| Sugar Beets | 2C,7G |
| Cotton | 5C,9G |
| PREEMERGENCE | |
| Morningglory | 3C,5H |
| Cocklebur | 2C,5H |
| Velvetleaf | 5C,9G |
| Nutsedge | 0 |
| Crabgrass | 0 |
| Barnyardgrass | 2C |
| Cheatgrass | 3G |
| Wild Oats | 3G |
| Wheat | 3G |
| Corn | 4C,7G |
| Soybean | 0 |
| Rice | 8H |
| Sorghum | 3C,8H |
| Sugar Beets | 4C,9G |
| Cotton | 5G |

What is claimed is:
1. A compound of the formula:

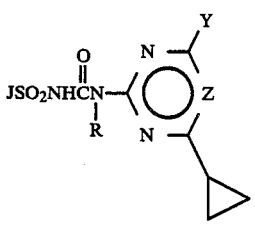

wherein

J is

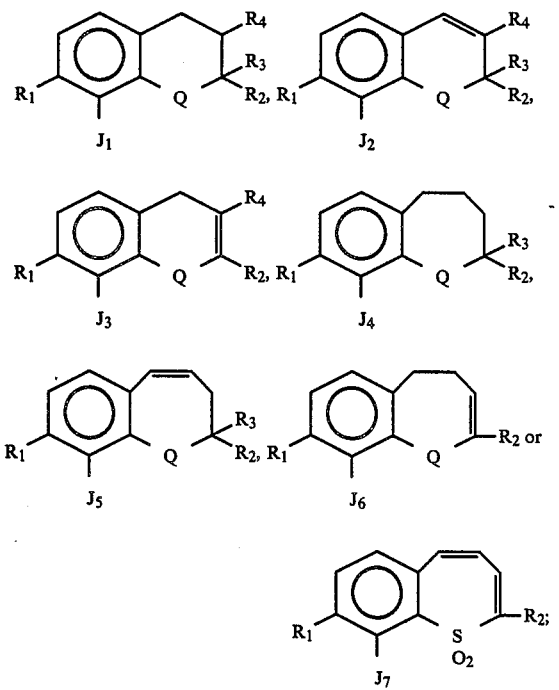

Q is O, S or SO$_2$;
R is H or CH$_3$;
R$_1$ is H, CH$_3$, OCH$_3$, Cl, Br, CO$_2$R$_5$, SO$_2$R$_6$, OSO$_2$R$_7$ or SO$_2$NR$_8$R$_9$;
R$_4$ is H or CH$_3$;
R$_2$ and R$_3$ are independently H or C$_1$-C$_3$ alkyl;
R$_5$ is C$_1$-C$_3$ alkyl, CH$_2$CH=CH$_2$, CH$_2$CH$_2$OCH$_3$ or CH$_2$CH$_2$Cl;
R$_6$ is C$_1$-C$_3$ alkyl;
R$_7$ is C$_1$-C$_3$ alkyl or CF$_3$;
R$_8$ and R$_9$ are independently C$_1$-C$_2$ alkyl;
Y is CH$_3$, OCH$_3$, OC$_2$H$_5$, CH$_2$OCH$_3$, NHCH$_3$ or N(CH$_3$)$_2$; and
Z is N;

and their agriculturally suitable salts; provided that:
(1) the total number of carbon atoms in R$_2$ and R$_3$ is less than or equal to 3;
(2) in Formula J$_2$, when R$_2$ and R$_3$ are other than H, then R$_4$ is H;
(3) in Formula J$_3$, when R$_2$ is other than H, then R$_4$ is H;
(4) when Q is S, then R$_1$ is not SO$_2$NR$_8$R$_9$;
(5) in Formulae J$_3$ and J$_6$, Q may not be O; and
(6) in Formula J$_7$, R$_1$ is not CH$_3$.

2. Compounds of claim 1 where J is J$_1$ or J$_4$.

3. Compounds of claim 2 where R is H and R$_1$ is H, CH$_3$, OCH$_3$, Cl, CO$_2$(C$_1$-C$_2$ alkyl) or SO$_2$(C$_1$-C$_2$ alkyl).

4. Compounds of claim 3 where Y is CH$_3$, OCH$_3$, OCH$_2$CH$_3$ or CH$_2$OCH$_3$.

5. Compounds of claim 4 where J is J$_1$, R$_1$ is H, CH$_3$, OCH$_3$ or Cl, and Y is CH$_3$ or OCH$_3$.

6. A composition suitable for controlling the growth of undesired vegetation which comprises an effective amount of a compound of claim 1 and at least one of the following: surfactant, solid or liquid diluent.

7. A composition suitable for controlling the growth of undesired vegetation which comprises an effective amount of a compound of claim 2 and at least one of the following: surfactant, solid or liquid diluent.

8. A composition suitable for controlling the growth of undesired vegetation which comprises an effective amount of a compound of claim 3 and at least one of the following: surfactant, solid or liquid diluent.

9. A composition suitable for controlling the growth of undesired vegetation which comprises an effective amount of a compound of claim 4 and at least one of the following: surfactant, solid or liquid diluent.

10. A composition suitable for controlling the growth of undesired vegetation which comprises an effective amount of a compound of claim 5 and at least one of the following: surfactant, solid or liquid diluent.

11. A method for controlling the growth of undesired vegetation which comprises applying to the locus to be protected an effective amount of a compound of claim 1.

12. A method for controlling the growth of undesired vegetation which comprises applying to the locus to be protected an effective amount of a compound of claim 2.

13. A method for controlling the growth of undesired vegetation which comprises applying to the locus to be protected an effective amount of a compound of claim 3.

14. A method for controlling the growth of undesired vegetation which comprises applying to the locus to be protected an effective amount of a compound of claim 4.

15. A method for controlling the growth of undesired vegetation which comprises applying to the locus to be protected an effective amount of a compound of claim 5.

* * * * *